United States Patent [19]
Ventura et al.

[11] Patent Number: 5,583,640
[45] Date of Patent: *Dec. 10, 1996

[54] FLAW HIGHLIGHTING LIGHT PANEL AND BOOTH FOR AUTOMOBILE BODY REPAIR

[75] Inventors: George Ventura, Bonner Springs, Kans.; James D. Jenkins, Lee's Summit; Winford D. McClain, Kansas City, both of Mo.

[73] Assignee: It's Dents Or Us, Inc., Overland Park, Kans.

[*] Notice: The term of this patent shall not extend beyond the expiration date of Pat. No. 5,436,726.

[21] Appl. No.: 506,440

[22] Filed: Jul. 24, 1995

Related U.S. Application Data

[63] Continuation-in-part of Ser. No. 247,640, May 23, 1994, Pat. No. 5,436,726.

[51] Int. Cl.⁶ .................................................. G01N 21/00
[52] U.S. Cl. ........................................... 356/371; 356/237
[58] Field of Search ................................... 356/237, 394, 356/371

[56] References Cited

U.S. PATENT DOCUMENTS

| | | | |
|---|---|---|---|
| 4,448,527 | 5/1984 | Milana | 356/237 |
| 4,629,319 | 12/1986 | Clarke et al. | 356/237 |
| 4,792,232 | 12/1988 | Jobe et al. | 356/394 |
| 5,090,804 | 2/1992 | Wong et al. | 356/237 |
| 5,168,322 | 12/1992 | Clarke et al. | 356/237 |
| 5,206,700 | 4/1993 | Reynolds et al. | 356/237 |
| 5,225,890 | 7/1993 | Lee et al. | 356/237 |
| 5,237,404 | 8/1993 | Tanka et al. | 356/376 |
| 5,367,378 | 11/1994 | Harding et al. | 356/371 |
| 5,414,518 | 5/1995 | Yazejian | 356/237 |
| 5,436,726 | 7/1995 | Ventura et al. | 356/371 |

FOREIGN PATENT DOCUMENTS

| | | |
|---|---|---|
| 269006 | 11/1988 | Japan . |
| 264448 | 10/1993 | Japan . |

OTHER PUBLICATIONS

Hugh W. Lippincott and Henry Stark; Optical–Digital Detection of Dents and Scratches on Specular Metal Surfaces; Aug. 15, 1982; *Applied Optics*, vol. 21, No. 16, pp. 2875–2881.

Photographs of dent highlighting panel (Attached as Exhibit A to Information Disclosure Statement) (no date).

*Primary Examiner*—Richard A. Rosenberger
*Attorney, Agent, or Firm*—Litman, McMahon and Brown, L.L.C.

[57] ABSTRACT

A light panel for highlighting flaws and imperfections in the surface of an automobile body or the like includes a pair of lenses with one lens positioned on each side of a light source. The lens on one side of the panel is yellow with a painted black stripe thereon with the black stripe irregularly "bleeding" into the yellow to create diverse shadow lines. The lens on the opposite side of the panel is white with a similar black stripes. Each black stripe includes a narrow centerline of white or black, respectively which serves as a reference. A fluorescent lamp is positioned between the lenses to project a shadow line light pattern onto the surface to be inspected for dents or imperfections. The white and black shadow line pattern is more effective at highlighting flaws in darker colored surfaces while the yellow and black shadow line pattern is more effective at highlighting flaws in lighter colored surfaces. A flaw highlighting booth for an automobile assembly plant or the like is made up of a plurality of such light panels positioned to form two arrays, with one array positioned on each side of automobile bodies on the assembly line to be examined. Each array has light panels oriented at varying angles such that a shadow line pattern is projected onto all areas of the automobile bodies to highlight any dents or imperfections therein. The floor of the booth can be painted with alternating white and black stripes as well.

30 Claims, 2 Drawing Sheets

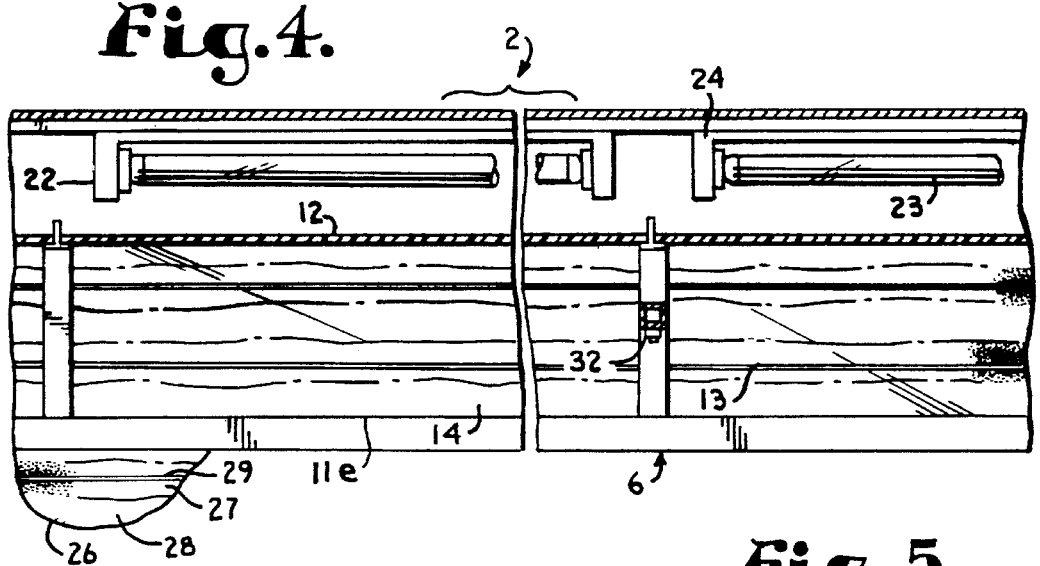
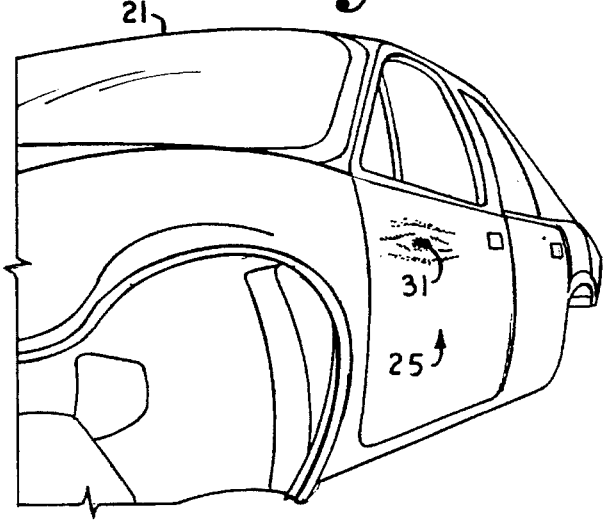
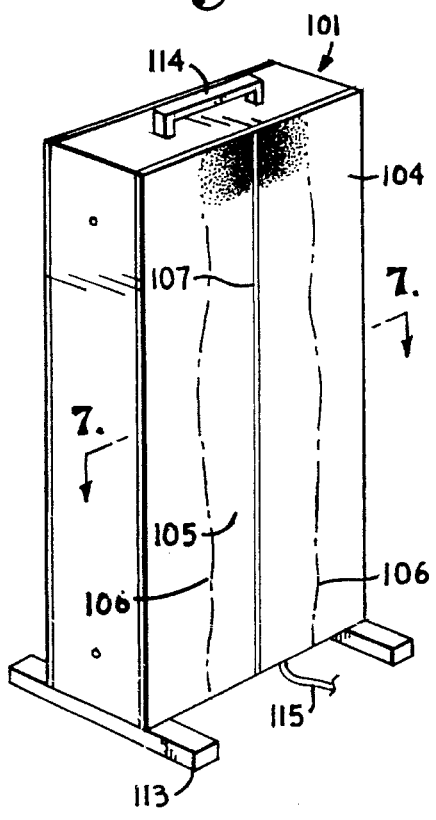
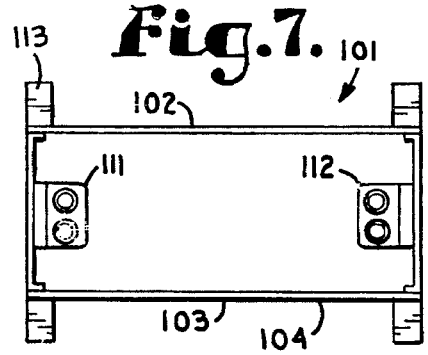

FLAW HIGHLIGHTING LIGHT PANEL AND BOOTH FOR AUTOMOBILE BODY REPAIR

CROSS REFERENCE TO RELATED APPLICATIONS

This application is a continuation of application Ser. No. 08/247,640, entitled FLAW HIGHLIGHTING LIGHT PANEL AND BOOTH FOR AUTOMOBILE BODY REPAIR, filed May 23, 1994, which issued as U.S. Pat. No. 5,436,726 on Jul. 25, 1995.

BACKGROUND OF THE INVENTION

I. Field of the Invention

The present invention relates to a light panel and booth for facilitating automobile body repairs, and, more specifically, to such a light panel and booth in which patterned light is projected onto an automobile body through specially designed and colored lenses to highlight automobile body flaws and imperfections.

II. Description of the Related Art

It is often difficult to detect small dents and other imperfections in the surface of an automobile body by unaided eyesight. This is particularly true of new or newly painted automobiles viewed under artificial light, such as in automobile assembly plants or repair and paint shops. In such assembly plants and repair shops, it is important that even the smallest dent or imperfection be detected to provide for satisfied customers and dealers and to avoid adversely affecting the reputation of the plant or shop.

Several previous efforts have been made to produce inspection systems for metal surfaces which are designed to detect surface dents and scratches. Hugh Lippincott and Henry Stark, in an article entitled "Optical-digital detection of dents and scratches on specular metal surfaces" in *Applied Optics,* Aug. 15, 1982, describe a system in which a regular grid pattern is reflected off of a metal surface to be inspected, with the reflected image photographed by a video camera. The photographs are then digitally analyzed and compared against samples from a calibration sample from an unflawed surface with any large deviations indicating the presence of one or more dents. For scratch detection, the authors describe a gray level threshold analysis to detect background to scratch brightness contrasts. The system described in the *Applied Optics* article was designed for and appears to be most suitable for implementation in an environment in which relatively small manufactured appliances must be inspected automatically, with badly scratched or dented samples simply discarded or recycled.

A series of U.S. Patents describe a retroreflective surface inspection system and method, including U.S. Pat. No. 4,629,319 to Clarke et al., U.S. Pat. No. 5,168,322 to Clarke et al., and U.S. Pat. No. 5,206,700 to Reynolds et al., all of which are assigned to Diffracto, Ltd. of Windsor, Canada. In these patents, light from a slit or point source is swept across a surface to be inspected via a scanning mirror or the like. The light reflects off of the inspected surface, off of a retroreflective surface and back off of the inspected surface and then to a camera lens or the eye of an observer. The retroreflected image received by the camera or eye magnifies any dents or imperfections in the surface being inspected. These systems employ sophisticated robotic inspectors and require complex synchronization of the swept beam and the analyzing equipment. For use in an automobile assembly plant or the like, the patents illustrate an inspection system with multiple independent light emitters, reflectors and analyzers. In addition, these patents describe an inspection process in which inspected panels must first be covered with a thin coating of oil to enhance their reflective properties. This is an expensive and time consuming process. Finally, in the Diffracto systems, as well as the Lippincott and Stark article, a sophisticated digital analysis must be performed and interpreted, which effectively limits the possibility of immediate correction of detected dents or other defects.

It is clear then, that an effective apparatus and method is needed for highlighting flaws and imperfections in automobile bodies. Such an apparatus and method should be inexpensive and reliable, should allow flaws and imperfections to be detected quickly and efficiently by an ordinary observer, should be effective at highlighting flaws in automobiles of a wide variety of colors and should allow detected dents and blemishes to be repaired immediately during the inspection process.

SUMMARY OF THE INVENTION

The present invention is directed to a portable light panel and a light booth for projecting light patterns onto an automobile body to facilitate inspection of the automobile body surface for flaws or imperfections.

The portable light panel includes a fluorescent backlight fixture enclosed between two diverse transparent lenses. The lens on one side is colored translucent white and has an opaque black stripe painted or otherwise applied thereon, with a narrow centerline left white. The lens on the opposite side is colored translucent yellow with a similar opaque black stripe painted thereon, again with a narrow centerline left as yellow. Depending upon the color of the automobile being inspected, one or the other side of the light box is turned toward the automobile to project a light pattern onto the automobile body surface.

The projected light pattern highlights the visibility of any flaws or imperfections in the body surface by magnifying an observer's perception of relative depth differences between the flaw and the unflawed body surface. The white lens side is used for automobiles with darker shades of color, such as black, navy blue, maroon, etc. while the yellow lens side is more effective at highlighting and enhancing imperfections in lighter colored automobiles, such as white, light gray, light blue, etc.

The black stripes are painted or otherwise applied to the yellow and white lenses in a fashion such that the black color irregularly "bleeds" into the yellow or white. This technique forms shadow areas between translucent yellow and opaque black, which shadow areas are projected onto the automobile by the backlights. The thus created shadow lines form light patterns on the automobile body which highlight any dents or imperfections in the automobile body surface by making the dents appear darker than the surrounding smooth surface, which appears to shine by contrast. The narrow centerlines are positioned to serve as a reference in aligning the light panel, i.e. the centerline projects a narrow strip of light within a dark band so that the dark band can be centered on a dent to be repaired.

The light panel booth is made up of a large plurality of light panels which are similar in construction to the portable light panel described above. The light panels are backlighted via fluorescent lamps and are positioned to form two arrays of panels with one array positioned on each side of an automobile to be inspected. In the case of an automobile assembly plant, automobile bodies which have been primed or "galvanized", are conveyed through the booth as an assembly line step, and, since a galvanized automobile body is a light gray color, the light panels preferably utilize yellow lenses. Light panels in the arrays are positioned at varying angles to best reflect off of different areas of the automobile bodies being inspected to highlight dents or imperfections at any point on the automobile bodies. As in the portable light panel, each dark stripe has a narrow centerline of light color to assist an observer in properly positioning himself such that a dark stripe is centered on a dent to be repaired.

OBJECTS AND ADVANTAGES OF THE INVENTION

The objects and advantages of the present invention include: providing a portable light panel which highlights flaws and imperfections in an automobile body surface; providing such a light panel which includes a specially colored lens or lenses which, when backlighted, project light patterns and shadow lines onto the automobile body which patterns highlight any imperfections in the surface; providing such a light panel which has a translucent white and opaque black striped lens on one side for highlighting surface flaws in darker colors and a translucent yellow and opaque black striped lens on the opposite side for highlighting surface flaws in lighter colors; providing a light panel booth made up of a plurality of light panels with alternating yellow and black striped lenses arrayed on opposite sides of an automobile to be examined; providing such a booth which highlights automobile body flaws and allows the reliable detection of such flaws as the automobile is being conveyed through the booth; providing such a light panel and booth in which the black stripes on the light panel lenses irregularly bleed into the lighter colors to provide shadow lines which form a portion of the light pattern projected onto the surface being inspected; providing such a portable light panel and booth in which each opaque black stripe includes a narrow centerline of translucent white or yellow to serve as a centerline reference; and providing such a light panel and light panel booth which is reliable, inexpensive and relatively simple to manufacture and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is an enlarged, fragmentary cross-sectional view of the light panel booth, taken along line 4—4 of FIG. 1, and including a portion of a floor painted with alternating light and black stripes.

FIG. 5 is an enlarged, fragmentary perspective view of a portion of the automobile body positioned in the booth and taken along line 5—5 of FIG. 1, illustrating a light pattern with shadow lines projected onto and reflected off of the body surface to highlight imperfections therein.

FIG. 6 is a perspective view of a portable light panel.

FIG. 7 is a cross-sectional view of the portable light panel, taken along line 7—7 of FIG. 6 and illustrating the orientation of opposite facing, differently colored lenses.

DETAILED DESCRIPTION OF THE INVENTION

Figure 1:
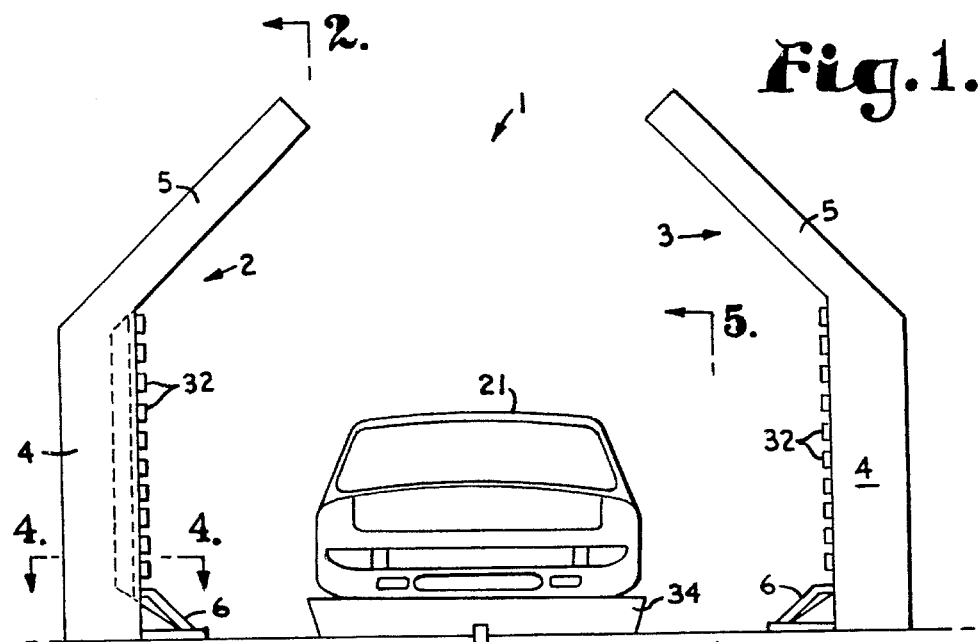
FIG. 1 is a perspective view of a light panel booth constructed in accordance with the present invention, with the booth positioned in an automobile assembly line, and with an automobile body positioned therein for inspection.
Figure 2:
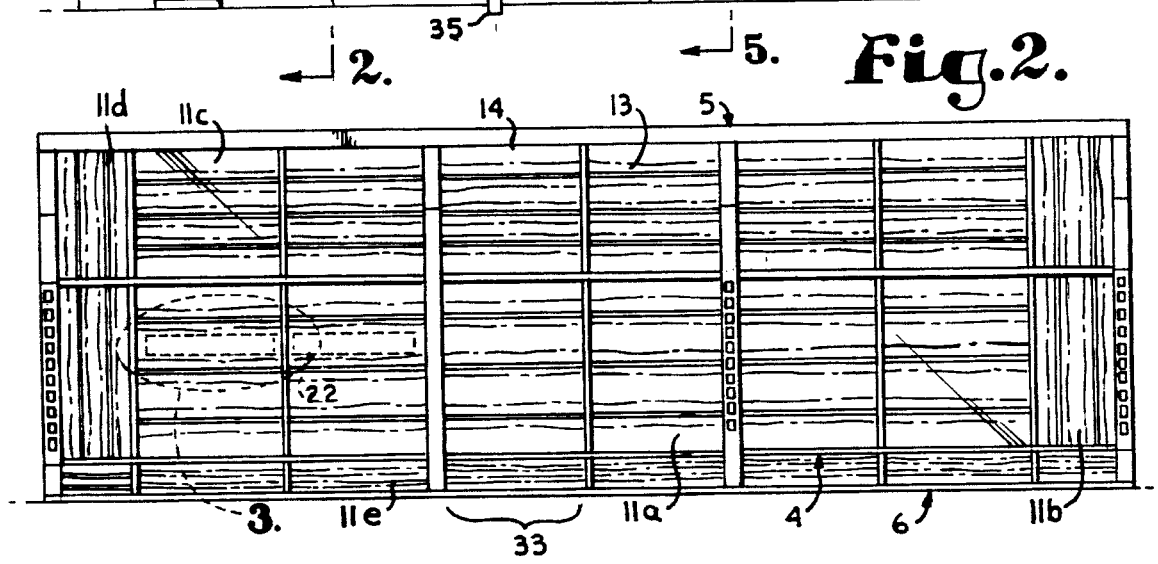
FIG. 2 is a front elevational view of one side of the light panel booth, taken along line 2—2 of FIG. 1.
Figure 3:
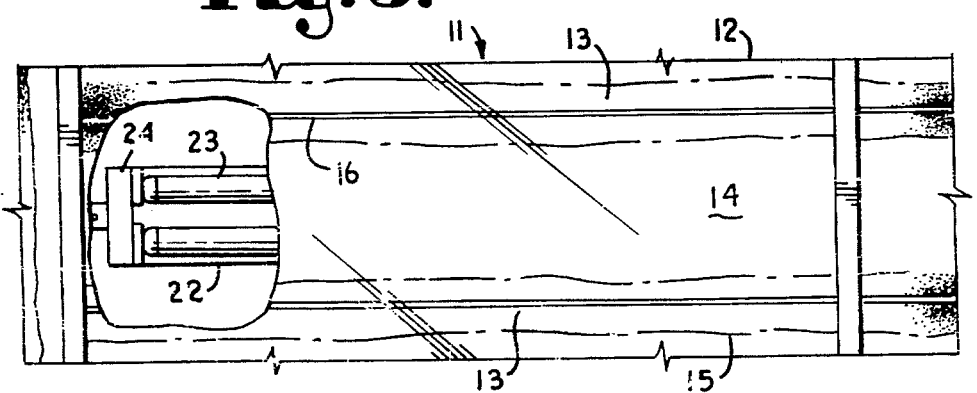
FIG. 3 is a greatly enlarged, fragmentary view of the portion of the light panel booth indicated in phantom lines in FIG. 2, with portions broken away to illustrate the placement of backlighting fluorescent lamps in a light panel.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in greater detail, and in particular to FIGS. 1–5, a light panel booth in accordance with the present invention is illustrated and is generally indicated with the numeral 1. The booth 1 includes a pair of opposing frameworks supporting respective light panel arrays 2 and 3, with each of the arrays 2 and 3 comprising a center, substantially vertical section 4, an upper, angled section 5 and a lower, angled section 6. Each of the sections 4–6 includes a bank of light panels 11, with a portion of one of the panels 11 illustrated in FIG. 3. Each panel 11 includes a light colored, translucent lens 12, with opaque dark stripes 13 periodically applied to the lens 12, leaving a centered, light colored band 14 positioned between each dark stripe 13. The borders between the light colored bands 14 and the black stripes 13 are not sharp lines, but instead are somewhat wavy and indistinct, with the black stripes 13 applied to the lenses 12 such that they bleed into the light bands 14 to form irregular shadow lines 15 therebetween. Each black stripe 13 includes a narrow centerline 16 therein, which centerline is masked off when painted so that the original color of the lens remains.

The center section 4 includes a number of interior panels, indicated as 11a, which are shown with their alternating stripes and bands 13 and 14, respectively, running substantially horizontally and a plurality of exterior panels 11b, which have their stripes 13 and 14 running substantially vertically. The upper section 5 also has a number of interior panels 11c, which are shown with their stripes and bands 13 and 14 extending substantially horizontally and a number of panels 11d which have their stripes and bands 13 and 14 running substantially vertically, albeit at the same angle as the upper section 5. Finally, the lower section 6 has a number of panels 11e, which are substantially longer than the panels in the center and upper section 4 and 5, respectively, and the panels 11e each have their stripes 13 and 14 running substantially horizontally. The vertical orientation of the panels 11b and 11d is optional, and was designed for certain car manufacturing plants in which vehicle bodies have portions, such as hoods and trunks, for example hanging vertically. In plants where there are no vertically oriented parts, all of the stripes 13 and 14 in the panels 11a–11e can be run horizontally. The orientations of the center section 4, the upper section 5, and the lower section 6 are designed to roughly correspond to the angular dimensions of an automobile body 21 to be inspected, with light patterns form the upper sections 5 projecting light patterns downward onto upper portions of the automobile body 21 and light patterns from the lower sections 6 being projected upward onto lower portions of the body 21.

Referring again to FIG. 3, each panel 11 includes a plurality of fluorescent lamp fixtures, such as the fixture 22, each with fluorescent bulbs 23 and ballasts 24 positioned behind each lens 12. In the preferred embodiment, there is one fixture 22 behind each light colored band 14 in each array 2 and 3. The fixtures 22 serve to backlight the lenses 12, thus casting an alternating light and dark optical image 25 onto the surface of the automobile body 21. This image 25 is reflected by the surface of the automobile body 21 to an observer (not shown). The somewhat irregular shadow line optical image 25 cast by the light panels 11 serves to highlight any dents or imperfections in the surface. This is due to the fact that incident light is reflected and modulated in an even and predictable fashion by a smooth, defect free surface while a dent or surface imperfection reflects and modulates the reflected light in a totally different fashion. Thus, to an observer, watching the shadow line pattern 25 reflected from the inspected surface, any dents are highlighted by the different observed optical modulation pattern surrounding the dent. FIG. 4 also illustrates a portion of a floor 26 which is painted white with spaced black stripes 27 painted thereon, leaving alternating white stripes 28 therein. Again, each black stripe 27 includes a narrow centerline 29 which is not painted, and the alternating black and white stripes serve to reflect ambient light in a pattern onto a lower surface of the automobile body 21.

FIG. 5 provides an illustration of the appearance of a reflected shadow line optical pattern 25 which surrounds a dent 31 in distinct contrast to the pattern reflected off of the smooth surface immediately surrounding the dent 31. This optical effect has a tendency to highlight or enhance an observer's perception of depth of a dent 31, and permits him to immediately straighten any dents 31 in the automobile body 21 while it is in the booth 1. When the dent 31 is straightened or smoothed, the effectiveness of the straightening exercise can be immediately observed as long as the automobile body 21 is still in the booth 1. The centerlines 16 and 29 serve to project narrow centered light bands in the middle of each black stripe of the pattern 25, which serve as reference lines, allowing an observer to correctly position his observation position to place an observed dent 31 in the middle of a projected black stripe.

A number of switches 32 are shown, with each switch 32 controlling one of more light fixtures 22 within a light panel 11. The booth 1 is comprised of a plurality of vertically stacked banks 33 of light panels 11. The switches 32 are shown in sufficient number for each light fixture 22 to be independently controlled, and this arrangement allows maximum flexibility in highlighting a particular area of the automobile bodies 21. However, for convenience it may be desirable for an entire bank of panels 11 or even an entire array 2 or 3 to be controlled via a single switch. Furthermore, while the switches 32 are illustrated as positioned on the front side of the arrays 2 and 3, it should be noted that they can also be positioned in a common switch panel located behind the arrays 2 and 3.

In FIG. 1, the automobile body 21 is shown attached to a conveyor carriage 34 which is part of an automobile assembly line 35. The booth 1 surrounds a portion of the assembly line 35, and is preferably positioned at a point in the manufacturing process just after the automobile body 21 has been primed or "galvanized". At this point, the primer coat is reflective enough that no additional treatment, such as the oil coating required in the prior art, is necessary for inspecting it within the booth 1. The booth 1 is preferably at least 30 feet in overall length, which allows workmen positioned within the booth 1 an opportunity to work out any dents 22 in the body 21 and reinspect them while the body 21 is still being conveyed through the booth 1. The arrays 2 and 3 are preferably positioned approximately 3–5 feet from the nearest surface of the automobile body 21 being inspected, depending upon the size of the automobile body 21. For the booth 1 positioned at this point in the assembly line, the panels 11a–11e preferably have yellow lenses 12 since the galvanized automobile bodies 21 have a uniform light gray color.

Referring to FIGS. 5 and 6, a single, portable light panel 101 is illustrated. The panel 101 is an enclosed box, but is otherwise similar to the panels 11 of FIGS. 1–4, but preferably includes opposite facing lenses 102 and 103. Each lens 102 and 103 is of a translucent, light color with a centered, opaque, dark colored stripe 105, which leaves a band 104 of the original light color. The light colored bands 104 on the lens 102 are preferably translucent yellow while the bands 104 on the lens 103 are preferably translucent white. The yellow lens 102 is more effective for inspection of lighter colored automobiles, such as white, light gray, silver, etc. while the white lens 104 is more effective for darker colored automobiles, such as dark gray, black, brown, etc. As in the panels 11 in the booth 1, the dark stripes 105 tend to bleed into the light bands, creating a wavy and indistinct shadow line 106 therebetween. A narrow centerline 107 of the original light color of each lens is left for a reference in centering a dent to be repaired in the dark stripe. A pair of backlighting fluorescent lamps 111 and 112 are positioned at either end of the enclosed panel 101. A number of legs 113 provide stability for the panel 101 when it is positioned on a floor and a handle 114 provides enhanced portability. Electrical power to the lamps 111 and 112 is provided via a cord 115.

The portable inspection light panel 101 is more suitable for use in automobile body shops, for example, where the auto bodies to be repaired are stationary. A workman who is to straighten a portion of an automobile body, such as a fender, for example, will position the panel 101 such that it shines an optical shadow line pattern onto the fender, with the projected centerline 107 centered in the dent to be repaired. The workman observes the light pattern reflected by the fender continuously while he straightens the dent. By constantly inspecting the fender as he straightens the dent, the workman is immediately aware of when the dent is straightened, or when further straightening is needed and he can immediately correct accordingly.

It is to be understood that while certain forms of the present invention have been illustrated and described herein, it is not to be limited to the specific forms or arrangement of parts described and shown.

What is claimed and desired to be secured by Letters Patent is as follows:

1. A light panel booth for highlighting defects in an object to be inspected, said object including at least two sides and a plurality of surfaces oriented at different angles, said booth comprising:

a. a first array of backlighted light panels directed toward one side of said object with different panels in said first array being oriented at respective different angles to accommodate the plurality of surfaces of said object, each light panel including a lens having at least one translucent light colored area adjacent to at least one opaque dark colored area, said light panels being positioned adjacent to each other to form said first array;

b. lighting means positioned behind said first array of light panels for backlighting said array to project a light pattern onto said surface to be inspected;

c. a second array of backlighted light panels directed toward a second side of said object, each said light panel in said second array also including a lens having at least one translucent light colored area adjacent to at least one opaque dark colored area, said light panels being positioned adjacent to each other to form said second array with different panels in said second array also being oriented at respective different angles to accommodate the plurality of surfaces of said object, and wherein said second array is positioned opposite said first array to form said booth; whereby d. said object to be inspected is positioned between said first and second arrays of light panels and said light pattern is projected onto said first and second sides of said object.

2. A light panel booth as in claim 1, wherein:

a. said opaque dark colored areas are applied to said lens in a manner such that the dark color bleeds into the light color to create shadow areas between the light colored areas and the dark colored areas such that shadow lines occur in said projected light pattern.

3. A light panel booth as in claim 1, wherein:

a. said lighting means comprises a plurality of fluorescent light fixtures, with each said light fixture positioned behind one of said lenses.

4. A light panel booth as in claim 1, wherein:

a. each of said opaque dark colored areas includes a narrow centerline of said translucent light color.

5. A light panel booth as in claim 4, wherein:

a. said translucent light color is yellow and said opaque dark color is black.

6. A light panel booth as in claim 5, wherein said surface to be inspected is an automobile body and said first array of light panels further comprises:

a. a second plurality of adjacent light panels positioned below said first plurality and oriented such that light from said second plurality of light panels is directed upward at an angle toward said automobile body.

7. A light panel booth as in claim 6, wherein said first array of light panels further comprises:

a. a third plurality of adjacent light panels positioned above said first plurality and oriented such that light from said third plurality of light panels is directed downward at an angle toward said automobile body.

8. A light panel booth as in claim 1, wherein said first array of light panels comprises:

a. a first plurality of adjacent light panels oriented in a substantially vertical plane.

9. A light panel booth as in claim 1, wherein said object to be inspected is an automobile body, said first and second panels being spaced apart a distance sufficient to allow said automobile body to be positioned therebetween.

10. A light panel booth as in claim 9, wherein each of said first and second arrays of light panels comprises:

a. a first plurality of adjacent light panels oriented in a substantially vertical plane;

b. a second plurality of adjacent light panels oriented to project light patterns at an upward angle and toward said automobile body, said second plurality of adjacent light panels being positioned below said first plurality; and c. a third plurality of adjacent light panels oriented to project light patterns at a downward angle toward said automobile body, said third plurality of adjacent light panels being positioned above said first plurality.

11. A light panel booth as in claim 9, wherein said booth further compress:

a. a floor, said floor also being painted with alternating light and dark areas.

12. A light panel booth for highlighting defects in the surface of an automobile body in an assembly line, said booth comprising:

a. a first array of backlighted light panels, each light panel including a lens having at least one translucent light colored area adjacent to at least one opaque dark colored area, said light panels being positioned adjacent to each other to form said first array;

b. a second array of backlighted light panels, each said light panel in said second array also including a lens having at least one translucent light colored area adjacent to at least one opaque dark colored area, said light panels being positioned adjacent to each other to form said second array, at least some of the light panels in both said first and second arrays being positioned at different respective angles to accommodate different surfaces of said automobile body, and wherein said second array is positioned opposite said first array to form said booth and said first and second arrays are positioned on opposite sides of said assembly line such that automobile bodies to be inspected are conveyed between said first and second arrays; and c. lighting means positioned behind said first and second arrays of light panels for backlighting said arrays to project a light pattern onto said automobile body surface.

13. A light panel booth as in claim 12, wherein:

a. said opaque dark colored areas are applied to each said lens in said first and second arrays in a manner such that the dark color bleeds into the light color to create shadow areas between the light colored areas and the dark colored areas such that shadow lines occur in said projected light pattern.

14. A light panel booth as in claim 12, wherein:

a. each of said opaque dark colored areas includes a narrow centerline of said translucent light color.

15. A light panel booth as in claim 12, wherein each of said first and said second arrays of light panels comprises:

a. a first plurality of adjacent light panels oriented in a substantially vertical plane;

b. a second plurality of adjacent light panels oriented such that light patterns are projected at an upward angle toward said assembly line, said second plurality of adjacent light panels being positioned below said first plurality; and c. a third plurality of adjacent light panels oriented such that light patterns are projected at a downward angle toward said assembly line, said third plurality of adjacent light panels being positioned above said first plurality.

16. A light panel booth as in claim 12, wherein:

a. said lighting means comprises a plurality of fluorescent light fixtures, with each said light fixture positioned behind one of said lenses.

17. A light panel booth as in claim 12, wherein:

a. said translucent light color is yellow and said opaque dark color is black.

18. A light panel booth as in claim 12, wherein said booth further compress:
   a. a floor, said floor also being painted with alternating light and dark areas.

19. A light panel for inspecting a surface for imperfections, said panel comprising
   a. a framework with first and second sides;
   b. a light source supported by and positioned on said framework between said first and second sides;
   c. a first lens at least partially covering said first side of said framework and said light source, said first lens including a first pattern with at least one translucent light colored area adjacent to at least one opaque dark colored area, said first lens projecting light from said light source in said first pattern onto said surface to be inspected, when said first lens is facing said surface, to highlight flaws and imperfections in said surface; and
   d. a second lens at least partially covering said second side of said framework and said light source, said second lens including a second pattern with at least one translucent light colored area adjacent at least one opaque dark colored area, said light colored areas in said second pattern being of a different color than those in said first pattern, said second lens also projecting light from said light source in said second pattern onto the surface to be inspected, when said second lens is facing said surface, to highlight flaws and imperfections in said surface.

20. A light panel as in claim 19, wherein:
   a. each of said dark areas in said first and second patterns is applied to the respective lens such that the dark color bleeds into the light colored areas to form shadow lines in said light patterns.

21. A light panel as in claim 19, wherein:
   a. each of said opaque dark colored areas includes a narrow centerline of said translucent light color.

22. A light panel as in claim 19, wherein:
   a. said first pattern includes alternating yellow and black areas.

23. A light panel as in claim 19, and wherein:
   a. said second pattern includes alternating white and black areas.

24. A light panel as in claim 19, and wherein:
   a. said lighting means comprises a fluorescent light fixture.

25. A light panel booth for highlighting defects in a surface to be inspected, said booth comprising:
   a. an array of light panels, each light panel including a lens with at least one translucent light colored area adjacent at least one opaque dark colored area, each of said opaque dark colored areas including a narrow centerline of said translucent light color, said light panels being positioned adjacent to each other to form said array; and
   b. lighting means positioned behind said first array of light panels for backlighting said array to project a light pattern onto said surface to be inspected.

26. A light panel booth as in claim 25, wherein:
   a. said opaque dark colored areas are applied to said lens in a manner such that the dark color bleeds into the light color to create shadow areas between the light colored areas and the dark colored areas such that shadow lines occur in said projected light pattern.

27. A light panel booth for highlighting defects in the surface of an automobile body in an assembly line, said booth comprising:
   a. a first array of light panels, each light panel including a lens having at least one translucent light colored area adjacent at least one opaque dark colored area, said light panels being positioned adjacent to each other to form said first array;
   b. a second array of backlighted light panels, each said light panel in said second array also including a lens having at least one light colored area adjacent at least one opaque dark colored area, said light panels being positioned adjacent to each other to form said second array, each of said opaque dark colored areas in said light panels in said first and second arrays including a narrow centerline of said translucent light color, said second array being positioned opposite said first array to form said booth and said first and second arrays being positioned on opposite sides of said assembly line such that automobile bodies to be inspected are conveyed between said first and second arrays; and
   c. lighting means positioned behind said first and second arrays of light panels for backlighting said arrays to project a light pattern onto said automobile body surface.

28. A light panel booth as in claim 27, wherein:
   a. said opaque dark colored areas are applied to each said lens in said first and second arrays in a manner such that the dark color bleeds into the light color to create shadow areas between the light colored areas and the dark colored areas such that shadow lines occur in said projected light pattern.

29. A light panel for inspecting a surface for imperfections, said panel comprising:
   a. a framework with first and second sides;
   b. a light source supported by and positioned on said framework between said first and second sides; and
   c. a lens at least partially covering said first side of said framework and said light source, said lens including a pattern with at least one translucent light colored area adjacent at least one opaque dark colored area, each of said opaque dark colored areas including a narrow centerline of said translucent light color, said lens projecting light from said light source in said pattern onto said surface to be inspected, when said lens is facing said surface, to highlight flaws and imperfections in said surface.

30. A light panel as in claim 29, wherein:
   a. said opaque dark colored areass are applied to said lens in a manner such that the dark color bleeds into the light colored areas such that shadow lines occur in said projected light pattern.

* * * * *